(12) United States Patent
Young et al.

(10) Patent No.: US 6,190,414 B1
(45) Date of Patent: *Feb. 20, 2001

(54) APPARATUS FOR FUSION OF ADJACENT BONE STRUCTURES

(75) Inventors: Wayne P. Young, Brewster, NY (US); Peter W.J. Hinchliffe, New Haven, CT (US)

(73) Assignee: Surgical Dynamics Inc., Norwalk, CT (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/741,796

(22) Filed: Oct. 31, 1996

(51) Int. Cl.[7] .................................... A61F 2/44

(52) U.S. Cl. .................... 623/17.15; 623/17.13; 623/17.16; 606/61

(58) Field of Search .................. 606/53, 60, 61, 606/69, 70, 71; 623/17, 18, 20, 17.13, 17.15, 17.16

(56) References Cited

U.S. PATENT DOCUMENTS

| | | |
|---|---|---|
| 3,486,505 | 12/1969 | Morrison . |
| 3,719,186 | 3/1973 | Merig, Jr. . |
| 3,848,601 | 11/1974 | Ma et al. . |
| 3,905,047 | 9/1975 | Long . |
| 3,916,907 | 11/1975 | Peterson . |
| 4,177,524 | 12/1979 | Grell et al. . |
| 4,309,777 | * 1/1982 | Patil ....................................... 623/17 |
| 4,484,570 | 11/1984 | Sutter et al. . |
| 4,501,269 | 2/1985 | Bagby . |

(List continued on next page.)

FOREIGN PATENT DOCUMENTS

| | | |
|---|---|---|
| 1961531 | 12/1969 | (DE) . |
| 3505567 | 2/1985 | (DE) . |
| 4109941 | * 10/1992 | (DE) ....................................... 623/17 |

(List continued on next page.)

OTHER PUBLICATIONS

Jose M. Otero Vich, "Anterior Cervical Interbody Fusion With Threaded Cylindrical Bone", *J. Neurosurg.*, 63:750–753, 1985.

(List continued on next page.)

*Primary Examiner*—Paul B. Prebilic (57) ABSTRACT

A prosthetic implant for facilitating fusion of adjacent vertebrae includes an implant member dimensioned to be at least partially positioned within an intervertebral space defined between adjacent vertebrae. The implant member includes first and second vertebral engaging plates operatively connected to each other for respectively engaging vertebral end plates of the adjacent vertebrae and having discontinuous surfaces to engage the vertebral end plates and promote bone ingrowth. A displacement member is associated with the engaging plates and is deployable to cause relative movement of the engaging plates to thereby at least laterally displace the engaging plates whereby in a deployed position the engaging plates are in supportive engaged relation with the adjacent vertebrae. The first and second engaging plates are preferably pivotally connected to each other at respective end portions thereof to define a reduced entry profile to facilitate insertion within the intervertebral space. The implant member may also define an interior cavity for accommodating bone growth inducing substances. The first and second engaging plates preferably include apertures extending therethrough to permit communication with the bone growth inducing substances within the interior cavity. The first and second engaging plates may also include projections for engaging the vertebral end plates to assist retention of the implant within the intervertebral space. An apparatus and method for facilitating fusion of adjacent vertebrae are also disclosed.

29 Claims, 10 Drawing Sheets

U.S. PATENT DOCUMENTS

| | | |
|---|---|---|
| 4,537,185 | 8/1985 | Stednitz . |
| 4,545,374 | 10/1985 | Jacobson . |
| 4,573,448 | 3/1986 | Kambin . |
| 4,611,582 * | 9/1986 | Duff ........................................ 606/61 |
| 4,677,972 | 7/1987 | Tornier . |
| 4,743,256 | 5/1988 | Brantigan . |
| 4,772,287 | 9/1988 | Ray et al. . |
| 4,820,305 | 4/1989 | Harms et al. . |
| 4,834,757 | 5/1989 | Brantigan . |
| 4,863,476 | 9/1989 | Shepperd . |
| 4,874,389 | 10/1989 | Downey . |
| 4,877,020 | 10/1989 | Vich . |
| 4,878,915 | 11/1989 | Brantigan . |
| 4,927,421 | 5/1990 | Goble et al. . |
| 4,936,848 | 6/1990 | Bagby . |
| 4,950,270 | 8/1990 | Bowman et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,064,425 | 11/1991 | Branemark et al. . |
| 5,139,499 | 8/1992 | Small et al. . |
| 5,147,402 | 9/1992 | Bohler et al. . |
| 5,171,278 | 12/1992 | Pisharodi . |
| 5,192,327 | 3/1993 | Brantigan . |
| 5,195,541 | 3/1993 | Obenchain . |
| 5,263,953 | 11/1993 | Bagby . |
| 5,290,312 * | 3/1994 | Kojimoto et al. .................... 623/17 |
| 5,300,076 | 4/1994 | Leriche . |
| 5,306,310 | 4/1994 | Siebels . |
| 5,313,962 | 5/1994 | Obenchain . |
| 5,354,302 | 10/1994 | Ko . |
| 5,357,983 | 10/1994 | Mathews . |
| 5,390,683 | 2/1995 | Pisharodi . |
| 5,395,317 | 3/1995 | Kambin . |
| 5,423,816 | 6/1995 | Lin . |
| 5,423,817 | 6/1995 | Lin . |
| 5,425,772 | 6/1995 | Brantigan . |
| 5,431,658 | 7/1995 | Moskovich . |
| 5,439,464 | 8/1995 | Shapiro . |
| 5,443,514 | 8/1995 | Steffee . |
| 5,443,515 | 8/1995 | Cohen et al. . |
| 5,445,639 | 8/1995 | Kuslich et al. . |
| 5,458,638 | 10/1995 | Kuslich et al. . |
| 5,458,642 * | 10/1995 | Beer et al. ........................... 623/17 |
| 5,484,437 | 1/1996 | Michelson . |
| 5,489,307 | 2/1996 | Kuslich et al. . |
| 5,489,308 | 2/1996 | Kuslich et al. . |
| 5,505,732 | 4/1996 | Michelson . |
| 5,522,899 * | 6/1996 | Michelson ........................... 623/17 |
| 5,534,031 | 7/1996 | Matsuzaki et al. . |
| 5,554,191 | 9/1996 | Lahille et al. . |
| 5,562,736 | 10/1996 | Ray et al. . |
| 5,571,109 | 11/1996 | Bertagnoli . |
| 5,571,189 | 11/1996 | Kuslich . |
| 5,571,192 | 11/1996 | Schönhöffer . |
| 5,653,763 * | 8/1997 | Errico et al. ......................... 623/17 |
| 5,658,335 * | 8/1997 | Allen .................................... 606/61 |
| 5,658,336 * | 8/1997 | Pisharodi ............................. 623/17 |
| 5,665,122 | 9/1997 | Kambin . |
| 5,782,832 * | 7/1998 | Larsen et al. ........................ 623/17 |

FOREIGN PATENT DOCUMENTS

| | | | |
|---|---|---|---|
| 4302397 | 1/1993 | (DE) . | |
| 4323595 | 7/1993 | (DE) . | |
| 0188954 * | 7/1986 | (EP) .................................... | 623/17 |
| 0307241 | 3/1989 | (EP) . | |
| 0551187 | 7/1993 | (EP) . | |
| 0567424 * | 10/1993 | (EP) .................................... | 623/17 |
| 0716840 | 6/1996 | (EP) . | |
| 0732093 | 9/1996 | (EP) . | |
| 0734703 | 10/1996 | (EP) . | |
| 2295729 | 12/1974 | (FR) . | |
| 2350824 | 3/1977 | (FR) . | |
| 2710519 | 9/1993 | (FR) . | |
| 5729348 | 2/1982 | (JP) . | |
| 58-78653 | 5/1983 | (JP) . | |
| 61-135652 | 6/1986 | (JP) . | |
| 62-164458 | 7/1987 | (JP) . | |
| 63-43654 | 2/1988 | (JP) . | |
| 1502402 | 8/1989 | (JP) . | |
| 1314560 | 12/1989 | (JP) . | |
| 8707827 | 12/1987 | (WO) . | |
| 8912431 | 12/1989 | (WO) . | |
| 9106261 | 5/1991 | (WO) . | |
| 9417759 | 8/1994 | (WO) . | |
| 9608205 | 3/1996 | (WO) . | |

OTHER PUBLICATIONS

Norman W. Hoover, "Methods of Lumbar Fusion", *The Journal of Bone and Joint Surgery*, vol. 50–A, No. 1, Jan. 1968, pp. 194–210.

Benjamin R. Wiltberger, "Intervertebral Body Fusion By the Use of Posterior Bone Dowel", pp. 69–79.

Parviz Kambin et al., "Percutaneous Lateral Discectomy of the Lumbar Spine", *Clinical Orthopaedics*, Apr. 1983, vol. 174, pp. 127–131.

Guy M. Sava et al., "Posterior Lumbar Interbody Fusion Made Simple", Neurological Surgery Associates of Cincinnati, Inc. CAGE CH: Lumbar Spacing Cages, *Scientix*.

Actualites Vertebrales, La Herni Discale Cervicale, No. 2, Avril 1994, pp. 1–11 Kiyoshi Kaneda and Isao Yamamoto, "Spinal Instrumentation Surgery In Lumbar and Lumbosacral Spine," *The Improvement of Medicine*, vol. 147, No. 14, Dec. 31, 1988.

Hiroshi Yamamoto, "Spinal Instrumentation For Lumbar Spine Segmental Transverse Wiring For Spondylolysis and Pedicular Screw–Spinal Plate For Spondylolisthesis," *The Improvement of Medicine*, vol. 145, No. 1, Apr. 2, 1988.

Kenichiro Shibata, Masayoshi Oga, Kazuo Hayashi, Yoichi Sugioka, "A New Contrivance of Anterior Spinal Fusion in Cervical Spine", *Orthopaedic and Traumatic Surgery*, vol. 35, No. 3, pp. 811–813, 1987.

Haruo Tsuji, "Anterior Body Fusion of Lumbar Spine Hernia," *Operation*, vol. 41, No. 11, pp. 1803–1811, 1987.

Hirotugu Oda, Shinya Kawai, Tetsuro Murakami, et al., "Osteoplastic Hemi/Bilateral Partial Laminectomy of Lumbar Spinal Hernia," *Operation*, vol. 41, No. 11, pp. 1785–1791, 1987.

Teiji Yano, et al., "Treatment of Spondylolisthesis By Posterior Fusion With Bone Grafting To Neutral Arch Defect," *Clinical Orthopaedic Surgery*, vol. 17, No. 4, pp. 394–399, 1982.

Toshihiko Yamane, et al., "A Case Report of Multiple Lumbar Spondylolyses With Spondylolisthesis," *Clinical Orthopaedic Surgery*, vol. 23, No. 3, pp. 311–314, 1988.

M. Maeshiro, K. Otani, K. Shibasaki, S. Nakai, K. Nemoto, M. Yoshida, "Posterior Fracture–Dislocation of the Thoracic Spine; Two Case Report," *Orthopedic Surgery*, vol. 39, No. 9, pp. 1373–1377, 1988–9.

Kunio Takaoka, "Clinical Application of Ceramic Implants in Orthopedics Surgery," *Medicina Philosophics*, vol. 4, No. 7, pp. 546–552, 1985.

Y. Yamano, Y. Mikawa, r. Watanabe, et al., "Anterior Body Fusion of Lumbar Degenerative Spondylolisthesis," *Journal of the Western Japanese Research Society For Spine*, vol. 13, pp. 46–50.

Dual Chisel and Its Bank Bones (Skimud Subkortikale Bones) For Posterior Lumbar Interbody Fusion—In Order To Simplify and Regularize the Surgical Procedure, *Orthopaedic Surgery*, vol. 11, pp. 150–3.

Vertebral Body Distraction System (Caspar), "*Orthopaedic Surgery*", vol. 11, pp. 135–9.

Takayoshi Ueda, et al., "Instrumentation Surgery of Lumbar Interbody Fusion," *Central Japan Journal of Orthopaedic & Traumatic Surgery*, pp. 87–89.

Haruo Tsuji, et al., "Development and Clinical Application of Artificial Intervertebral Disc For Cervical Disc Lesions," *Central Japan Journal of Orthopaedic & Traumatic Surgery*, pp. 1505–1506.

* cited by examiner

APPARATUS FOR FUSION OF ADJACENT BONE STRUCTURES

BACKGROUND

1. Technical Field

The present disclosure relates generally to a surgical apparatus for fusing adjacent bone structures, and, more particularly, to an apparatus and method for fusing adjacent vertebrae.

2. Background of the Related Art

The fusion of adjacent bone structures is commonly performed to provide for long-term replacement to compensate for degenerative or deteriorated disorders in the disc. For example, an intervertebral disc, which is a ligamentous cushion disposed between adjacent vertebrae, may undergo deterioration as a result of injury, disease, tumor or other disorders. The disk shrinks or flattens leading to mechanical instability and painful disc translocations or herniation.

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. For example, U.S. Pat. No. 4,877,020 to Vich discloses a cylindrical bone plug having a thread on its exterior, which is screwed into a correspondingly dimensioned cylindrical bore drilled in the intervertebral space. Other bone grafting plugs are disclosed in U.S. Pat. No. 4,950,296.

More recently, emphasis has been placed on fusing bone structures (i.e., adjoining vertebrae) with prosthetic cage implants. One fusion cage implant is disclosed in U.S. Pat. No. 5,026,373 to Ray et al. The Ray '373 fusion cage includes a cylindrical cage body having a thread formed as part of its external surface and apertures extending through its wall which communicate with an internal cavity of the cage body. The fusion cage is inserted within a tapped bore or channel formed in the intervertebral space thereby stabilizing the vertebrae and maintaining a pre-defined intervertebral space. The adjacent vertebral bone structures communicate through the apertures with bone growth inducing substances within the internal cavity to unite and eventually form a solid fusion of the adjacent vertebrae. Other prosthetic implants are disclosed in U.S. Pat. Nos. 4,501,269, 4,961,740, 5,015,247 and 5,489,307.

Both anterior (transabdominal) and posterior surgical approaches are used for interbody fusions of the lumbar spine. Fusions in the cervical area of the spine are primarily performed using a posterior approach. Typically, a plug or fusion cage of the type discussed above is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancellous region to facilitate bone ingrowth across the implant.

More recently, laparoscopic procedures, i.e., an anterior approach through the abdominal cavity, are being utilized to access the spine to perform the discectomy and subsequent fusion procedures. In laparoscopic surgical procedures, the abdominal cavity is insufflated with $CO_2$ gas. A surgical trocar which includes a cannula and an obturator positioned within the cannula is applied against the abdominal cavity. The whole assembly is advanced in the abdominal cavity to gain access thereto. The obturator is removed to permit the introduction of surgical instruments within the cannula to perform the desired procedure. The laparoscopic approach is characterized by being less invasive to the patient resulting in less patient trauma and improved recovery time.

The laparoscopic approach for discectomy and spinal fusion requires specialized instrumentation to effectively position the implant within the remotely located and relatively inaccessible intervertebral space.

SUMMARY

Accordingly, the present disclosure is directed to a spinal fusion apparatus particularly suited for use in conjunction with laparoscopic or minimally invasive techniques utilized in performing discectomy and spinal fusion. In one preferred embodiment of the disclosure, a prosthetic implant for facilitating fusion of adjacent vertebrae is disclosed. The prosthetic implant includes an implant member dimensioned to be at least partially positioned within an intervertebral space defined between adjacent vertebrae. The implant member includes first and second vertebral engaging plates operatively connected to each other for respectively engaging vertebral end plates of the adjacent vertebrae and having discontinuous surfaces to engage the vertebral end plates and promote bone ingrowth. A displacement member is associated with the engaging plates and is deployable to cause relative movement of the engaging plates to thereby at least laterally displace the engaging plates whereby in a deployed position the engaging plates are in supportive engaged relation with the adjacent vertebrae.

The first and second engaging plates are pivotally connected to each other at respective end portions thereof to define a reduced entry profile to facilitate insertion within the intervertebral space. The implant member may also define an interior cavity for accommodating bone growth inducing substances. The first and second engaging plates preferably include apertures extending therethrough to permit communication with the bone growth inducing substances within the interior cavity. The first and second engaging plates may also include projections for engaging the vertebral end plates to assist retention of the implant within the intervertebral space.

The preferred displacement member is a telescoping jack member which is deployable with a remotely operable applier instrument. The telescoping jack member includes a screw jack having a threaded portion which is cooperatively engageable with a threaded component. The screw jack and the threaded component are disposed between the engaging plates of the implant whereby rotational movement of one of the screw jack and the threaded component causes corresponding telescoping motion of the screw jack and displacing movement of the first and second engaging plates.

The present disclosure is also related to an apparatus for facilitating fusion of adjacent vertebrae. The apparatus includes an elongated member having proximal and distal ends and defining a longitudinal axis, an implant member releasably mounted to the distal end of the elongated member and a manually operable actuator operatively connected to the implant member and moveable to deploy the implant member. The implant member is configured for insertion within an intervertebral space defined between adjacent vertebrae and has first and second vertebral engaging plates adapted for relative movement between a retracted position and an extended position. The first and second engaging plates define an internal cavity for reception of bone growth inducing substances and have contacting surfaces with apertures extending therethrough for communicating with the internal cavity.

The manually operable actuator is operatively connected to a displacement mechanism which moves the implant member between the retracted and extended positions upon movement of the actuator. The displacement mechanism includes a telescopic jack member disposed between the engaging plates and adapted for telescoping movement to deploy the implant.

The present disclosure is also directed to a method for facilitating spinal fusion of adjacent vertebrae. The method includes accessing the intervertebral space defined between adjacent vertebrae, introducing a fusion implant within the intervertebral space and having first and second vertebral contacting plates defining discontinuities to promote bone ingrowth, causing relative movement of the first and second contacting plates such that the contacting plates supportingly engage the adjacent vertebrae, and permitting bone growth into the discontinuities of the vertebral contacting plates to form a solid fusion. Preferably, the implant is deployed with a remotely operable actuator instrument

BRIEF DESCRIPTION OF THE DRAWINGS

Preferred embodiment(s) of the present disclosure are described herein with reference to the drawings wherein.

DETAILED DESCRIPTION OF THE PREFERRED EMBODIMENT(S)

The apparatus of the present disclosure is intended for fusing adjacent bone structures and has particular application in the spinal fusion of adjacent vertebrae subsequent to a discectomy procedure. The apparatus is strategically adapted for application during minimally invasive or endoscopic surgical techniques currently being utilized to carry out discectomy procedures. It is envisioned, however, that the spinal fusion apparatus may be implanted utilizing more conventional anterior and/or posterior surgical approaches as well.

Figures 1, 2:
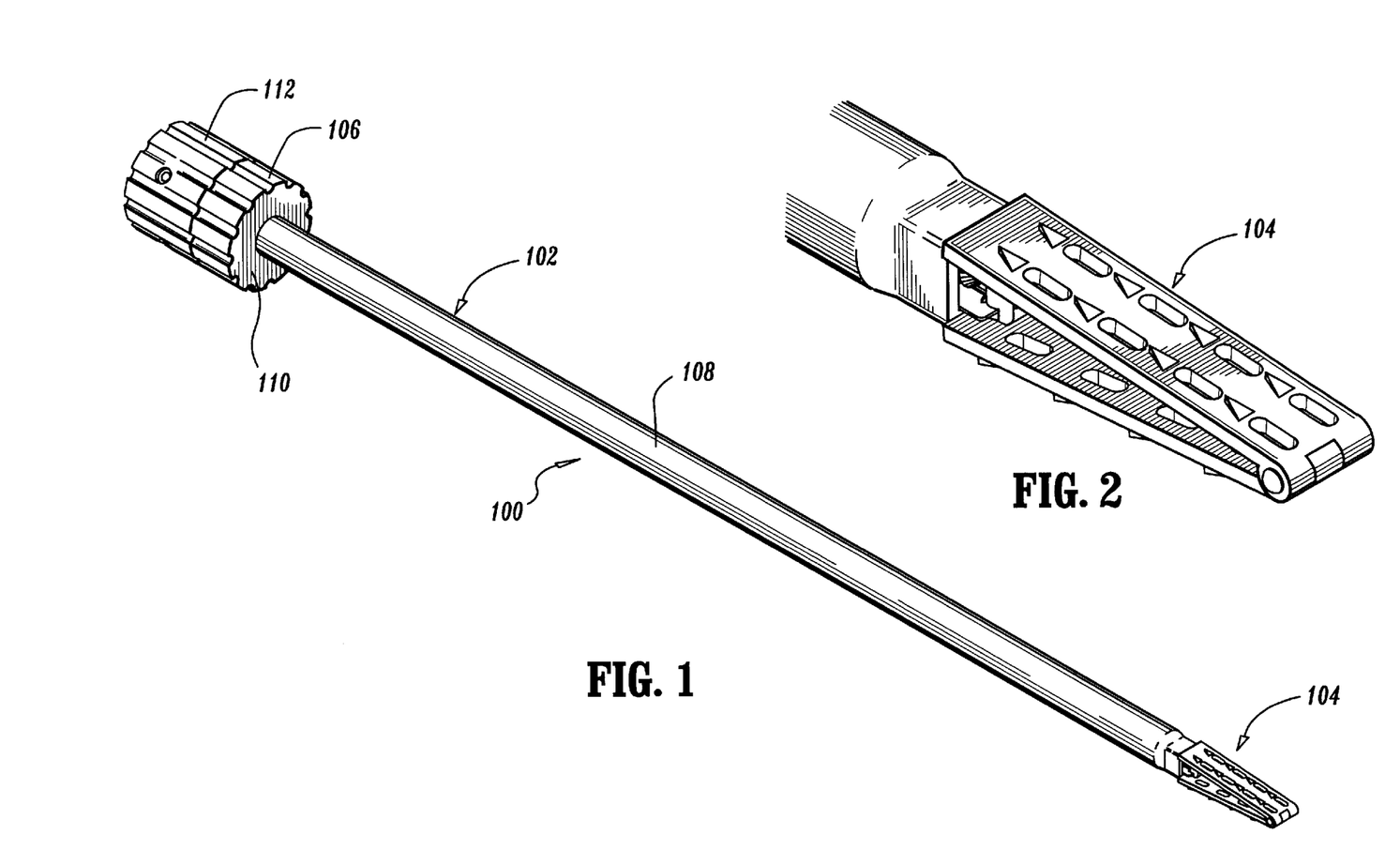
FIG. 1 is a perspective view of the apparatus in accordance with the principles of the present disclosure illustrating the fusion implant applicator and the fusion implant mounted to the distal end of the applicator.
FIG. 2 is an enlarged perspective view of the fusion implant of the apparatus.

Referring now to FIGS. 1–2, there is illustrated the apparatus in accordance with the principles of the present disclosure. Apparatus 100 includes applier instrument 102 and implant member 104 releasably mounted to the applier instrument 102. Applier instrument 102 is adapted to insert and deploy implant member 104 as will be discussed below. Applier instrument 102 is generally elongated for endoscopic application.

Figure 3:
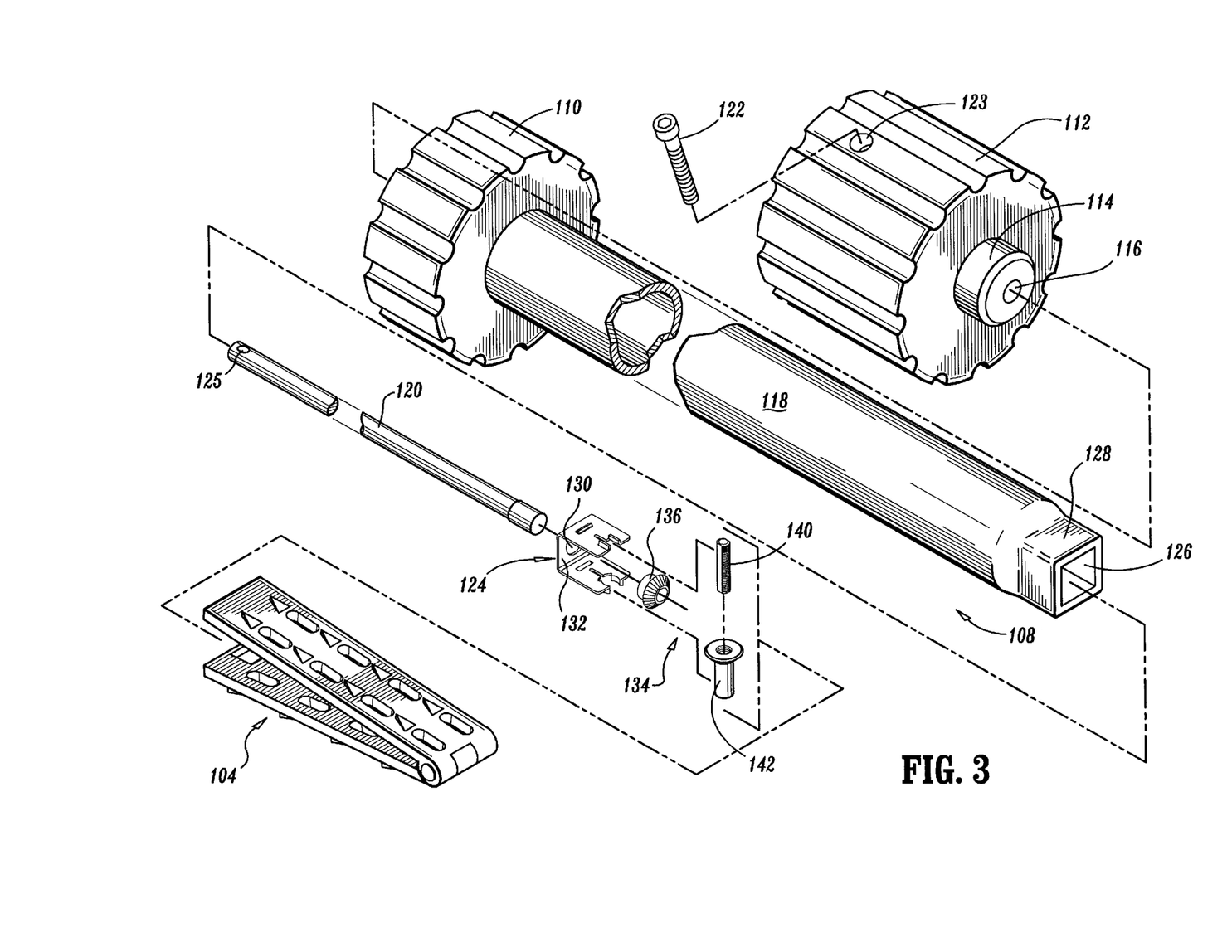
FIG. 3 is a perspective view with parts separated of the apparatus of FIG. 1.
Figures 4, 5, 6, 7:
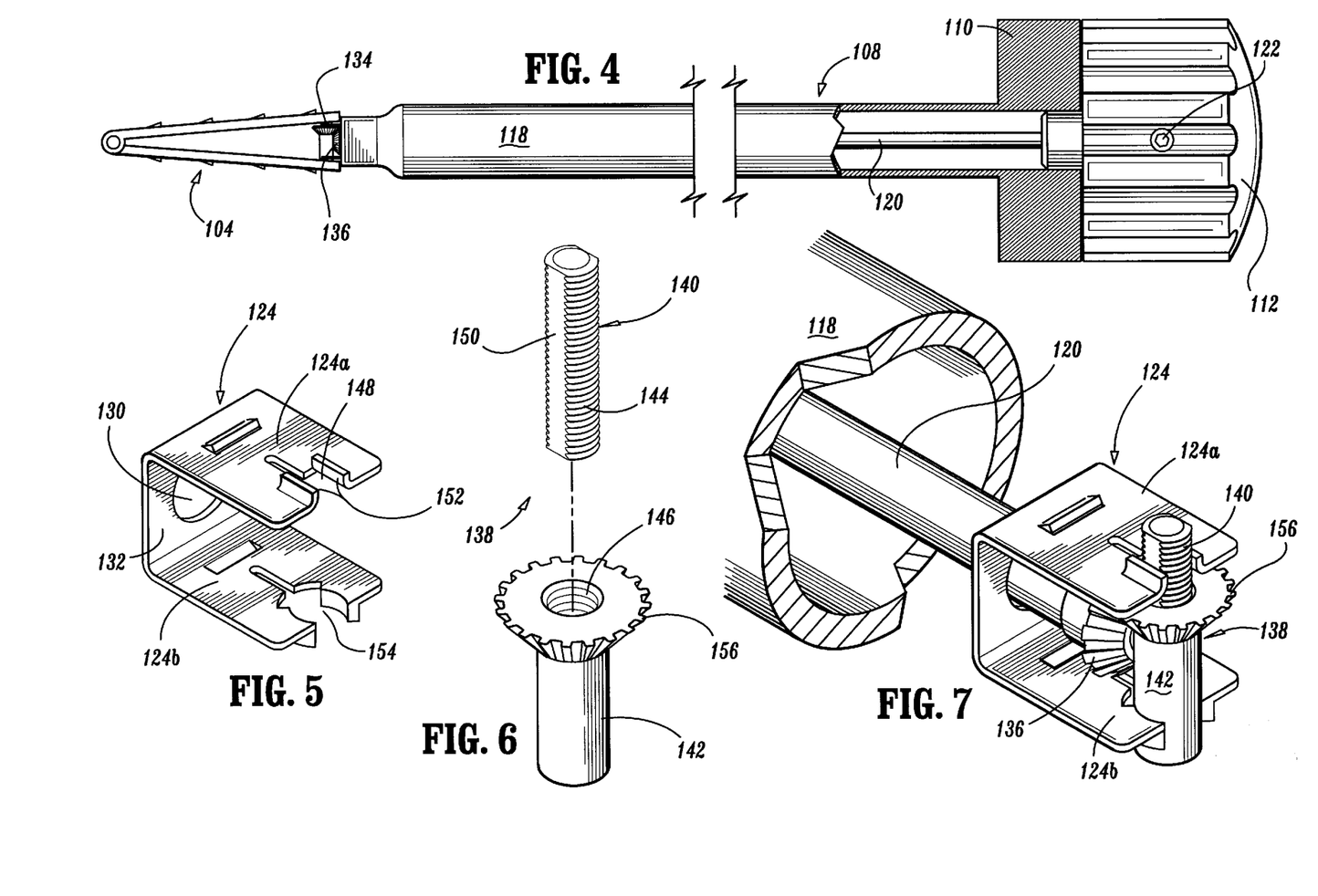
FIG. 4 is a side plan view in partial cross-section of the apparatus.
FIG. 5 is an enlarged perspective view of the mounting clamp of the applicator for releasably mounting the fusion implant to the applicator.
FIG. 6 is a perspective view of the telescopic jack mechanism for deploying the fusion implant.
FIG. 7 is a perspective view with a portion cut-away of the distal end of the applicator illustrating the telescopic jack mechanism and the mounting clamp.

With reference now to FIGS. 3–4, in conjunction with FIGS. 1–2, applier instrument 102 includes handle 106 and elongated or endoscopic portion 108 extending distally from the handle 106. Handle 106 includes proximal frame 110 and control knob 112 rotatably mounted relative to the frame 110. Control knob 112 has distal cylindrical mounting portion 114 which functions in rotatably mounting the control knob 112 to frame 110. More particularly, mounting portion 114 is received within a correspondingly dimensioned inner bore formed in the interior of frame 110 in intermitting relation as best depicted in FIG. 4 and is advantageously dimensioned to rotate within the inner bore thereby permitting control knob 112 to rotate relative to frame 110. Control knob 112 may possess an outer scalloped surface to facilitate user engagement. Mounting portion 114 further defines an axial bore 116 extending therethrough.

The components of handle 106 are preferably fabricated from a rigid material such as aluminum alloy, stainless steel or a suitable polymeric material. Endoscopic or elongated portion 108 consists of outer sleeve 118 and deployment shaft 120 coaxially mounted within the outer sleeve 118. Outer sleeve 118 may be integrally formed with frame 110 as shown, or, alternatively, may be a separate component which is mounted to the frame 110 by conventional means. Deployment shaft 120 is accommodated at its proximal end within axial bore 116 of control knob 112. Deployment shaft 120 is fixedly secured to control knob 112 of handle 106 such that rotational movement of the control knob 112 causes corresponding rotational movement of the deployment shaft 120. In a preferred embodiment, screw means 122 traversing openings 123, 125 in control knob 112 and deployment shaft 120, respectively, are utilized to effect securement of deployment shaft 120 to control knob 112. Other means for securement are envisioned as well such as with the use of adhesives, etc.

Referring now to FIGS. 3–5, elongated portion 108 has mounting clamp 124 mounted at its distal end for mounting implant member 104 to applier instrument 102. Mounting clamp 124 defines a generally rectangular configuration and is inserted within a correspondingly dimensioned rectangular shaped bore 126 (FIG. 5) of mounting portion 128 defined at the distal end of outer sleeve 118. Mounting clamp 124 may be secured within the bore 126 by conventional means e.g., friction fit adhesives, etc. Mounting clamp 124 has aperture 130 in transverse plate 132 (FIG. 5) which receives the distal end of deployment shaft 120. Aperture 130 is correspondingly dimensioned to permit rotational movement of deployment shaft 120 therein.

With reference now to FIGS. 3–8, a displacement mechanism, identified generally as reference numeral 134, is mounted within mounting clamp 124. The displacement mechanism includes two components, namely, spur gear 136 and telescopic jack mechanism 138 which is depicted in FIG. 6. Spur gear 136 is fixedly mounted to the distal end of deployment shaft 120 and rotates in response to rotational movement of the deployment shaft 120. Telescopic jack mechanism 138 incorporates telescopic jack screw 140 and rotatable component 142. Telescopic jack screw 140 is in threaded engagement with rotatable component 142 through the cooperation of the external threaded portion 144 and internal threaded portion 146 (FIG. 6) of the jack screw 140 and the rotatable component 142, respectively.

Telescopic jack mechanism 138 is releasably mounted to mounting clamp 124. In a preferred embodiment, jack screw 140 is received within rectangular recess 148 defined in upper plate 124a of the mounting clamp 124 (FIG. 5). Jack screw 140 has opposed planar surfaces 150 (FIG. 6) which contact corresponding inner surfaces 152 defined by recess 148. In this manner, jack screw 140 is prevented from rotating relative to mounting clamp 124, but, is permitted to translate vertically within the mounting clamp 124 thereby opening the implant 104 as will be discussed.

Figure 8:
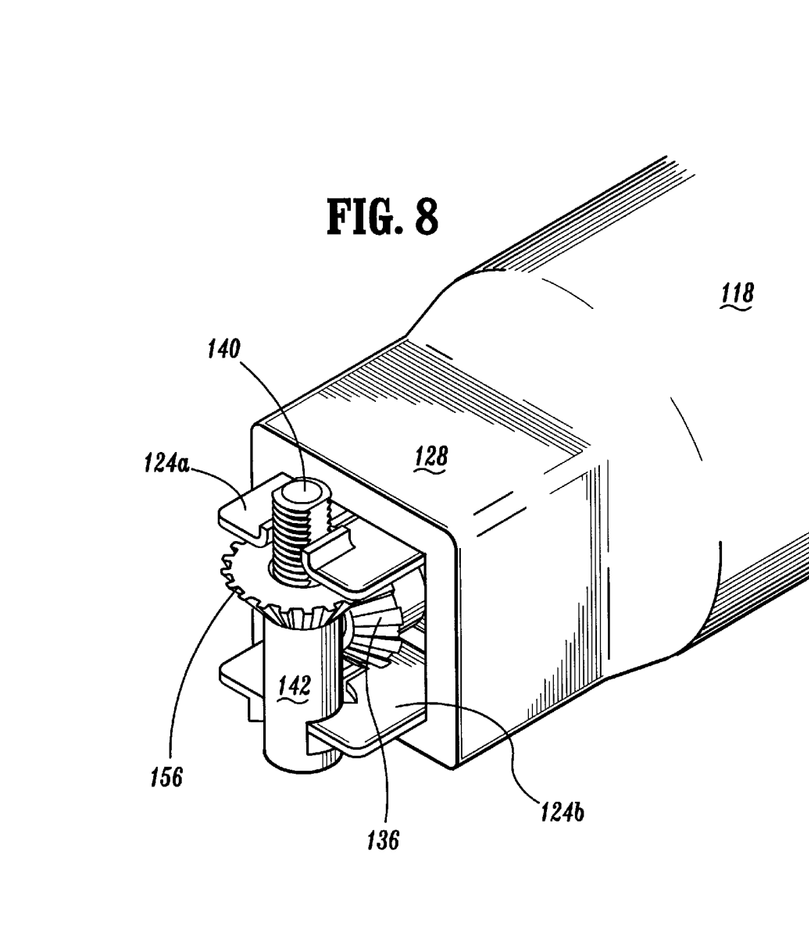
FIG. 8 is a perspective view of the distal end of the applicator further illustrating the telescopic jack mechanism and the mounting clamp.

Rotatable component 142 has a generally circular cross-section and is received within arcuate recess 154 defined in lower plate 124b of mounting clamp 124. Arcuate recess 154 is strategically dimensioned to permit rotational movement of rotatable component 142 therewithin. As best depicted in FIGS. 6–8 rotatable component 142 incorporates a spur gear 156 at its upper end. Spur gear 156 of rotatable component 142 threadably engages spur gear 136 mounted to the distal end of deployment shaft 120. As a result, rotational movement of deployment shaft 120 and spur gear 136 causes rotatable component 142 to rotate accordingly.

Figure 9:
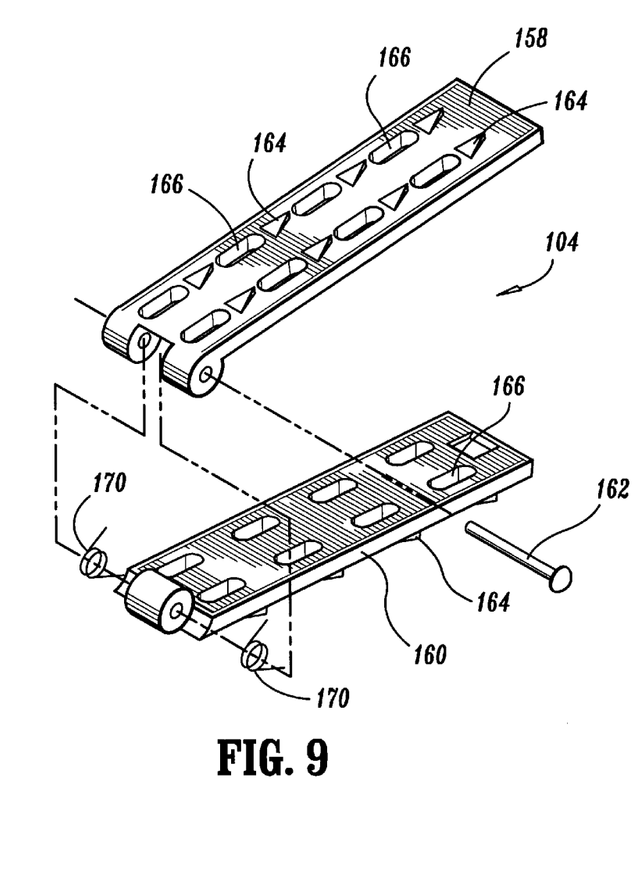
FIG. 9 is a perspective view with parts separated of the fusion implant illustrating its vertebral engaging plates.
Figure 10:
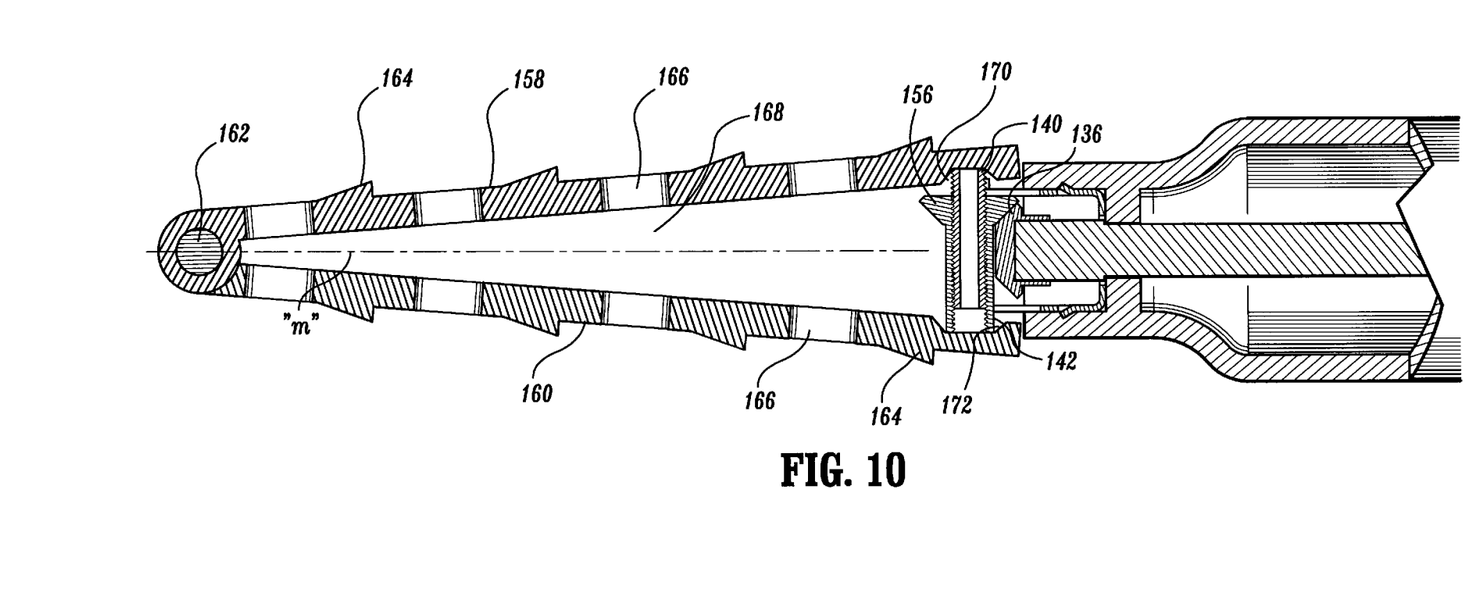
FIG. 10 is an enlarged cross-sectional view of the distal end of the applicator and the fusion implant illustrating the relationship of the deployment shaft of the applicator and the telescopic jack mechanism of the fusion implant.

Referring now to FIGS. 9–10, implant member 104 of the apparatus 100 will be discussed. Implant member 104 includes first and second engaging plates 158, 160 pivotally mounted at one end portion about pivot pin 162. Engaging plates 158, 160 have discontinuous surfaces which engage the adjacent bone tissue, e.g., vertebral end plates, to promote bone ingrowth. In particular, engaging plates 158, 160 each includes a plurality of triangular projections 164 which define teeth to engage the adjacent bone structures to resist tendency of the implant 104 to move or become dislodged once positioned within the adjacent bone structures. Engaging plates 158, 160 further include a plurality of openings 166 extending therethrough which communicate with interior cavity 168 (FIG. 10) defined between the engaging plates 158, 160. Engaging plates 158, 160 are spring biased to a normal closed position by torsion springs 170 wrapped about pivot pin 162. Implant member 104 defines a reduced profile at its leading (distal) end to facilitate introduction within the intervertebral space. The implant member defines a longitudinal plane "m" extending between engaging plates 158, 160 in general equidistant relation therewith.

As best depicted in FIG. 10, in the mounted condition of implant member 104 to applier instrument 102, telescopic jack mechanism 138 is disposed between engaging plates 158, 160 with jack screw 140 contacting the inner surface of upper engaging plate 158 and rotatable component 142 contacting the inner surface of lower engaging plate 160. Preferably, jack screw 140 and rotatable component 142 are received within corresponding recesses 170, 172 define within the inner surfaces of the respective engaging plates 158, 160. It is to be noted that torsional springs 170 exert sufficient force to retain telescopic jack mechanism 138 between engaging plates 158, 160, i.e., the springs 170 bias plates 158, 160 to a closed position. The upper end face of jack screw 140 may be secured to upper engaging plate 158 if desired to further facilitate retention of telescopic jack mechanism 138 within implant 104.

Operation

The use of the apparatus of the present disclosure in conjunction with a laparoscopic approach for lumbar discectomy will now be discussed. In accordance with laparoscopic surgical techniques, the abdominal cavity is insufflated with $CO_2$ gas. A surgical trocar having a cannula and an obturator which is positionable within the cannula is applied against the abdominal cavity. The whole assembly is advanced into the abdominal cavity to gain access thereto. The obturator is removed to permit the introduction of surgical instruments within the cannula to perform the desired procedure, in this case, a laparoscopic discectomy. Discectomy involves removal of at least a portion of the degenerated disc material with the use of endoscopic cutting instruments (not shown) e.g., scalpels, ronguers. One endoscopic cutting instrument suitable for removing disc material during a laparoscopic discectomy procedure is disclosed in commonly assigned U.S. patent application Ser. No. 08/528, 268 filed Sep. 14, 1995, the contents of which are incorporated herein by references.

Figure 11:
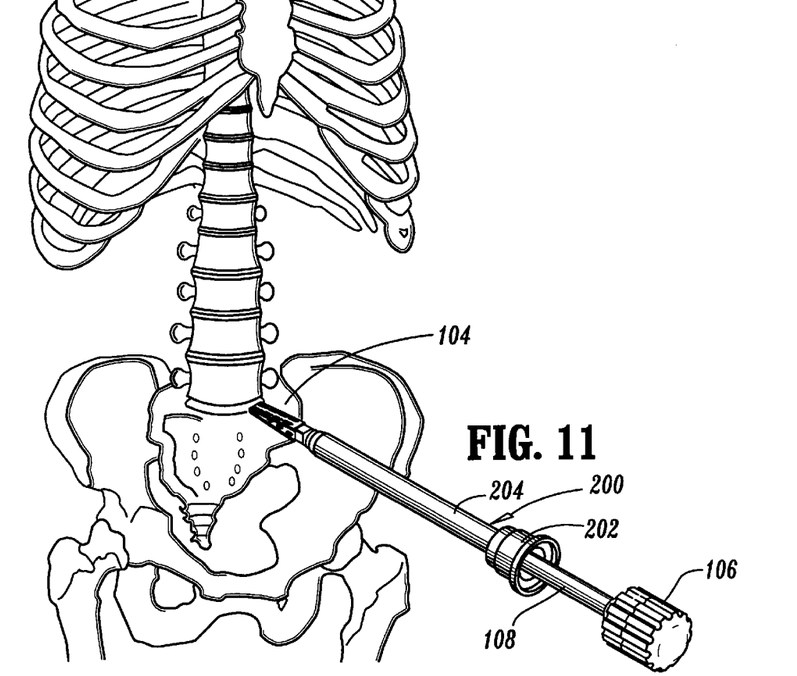
FIG. 11 is a view illustrating the laparoscopic insertion of the apparatus subsequent to a discectomy procedure.
Figure 12:
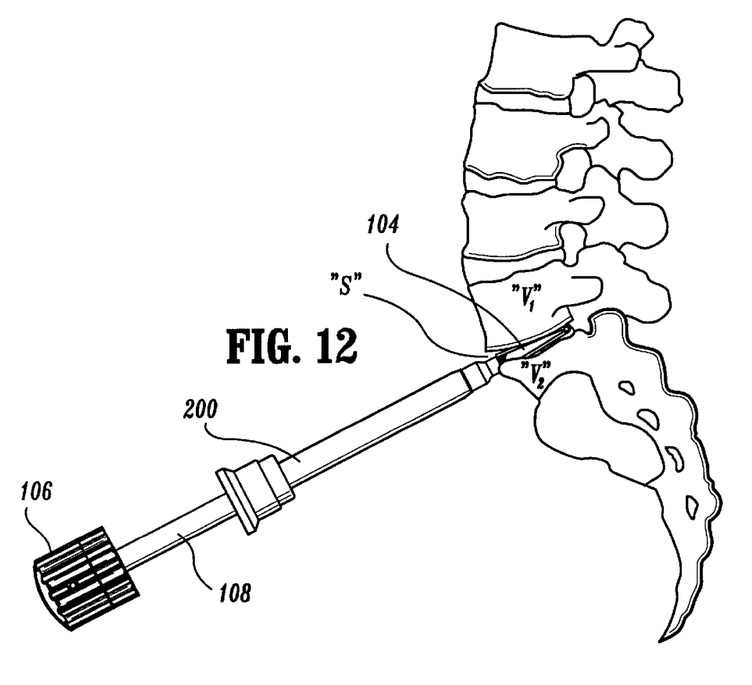
FIG. 12 is a view illustrating positioning of the fusion implant of the apparatus within an intervertebral space defined between adjacent vertebrae.

Once the discectomy is performed, attention is directed to inserting the implant member 104 of the apparatus 100 within the intervertebral space. With reference now to FIG. 11 which depicts a conventional cannula 200 (having cannula housing 202 and cannula sleeve 204) accessing insufflated abdominal cavity, apparatus 100 is inserted through cannula 200 and advanced to a position adjacent the desired intervertebral space. At this point in the procedure, the interior cavity 168 (FIG. 10) of implant member 104 may be packed with bone growth inducing substances "b" such as bone chips or cancellous bone taken from the iliac crest as is conventional in the art. In the alternative, the bone growth material may be packed within the implant member 104 before its placement into the body cavity to minimize operative steps within the body cavity. With reference to FIG. 12, implant member 104 is thereafter positioned with the assistance of applicator instrument 102 within the targeted intervertebral space "s" defined between adjacent vertebrae $V_1$, $V_2$. As stated above, the reduced profile as presented by the leading end of implant member 104 facilitates positioning of the implant member 104 within the adjacent vertebrae $V_1$, $V_2$.

Figure 13:
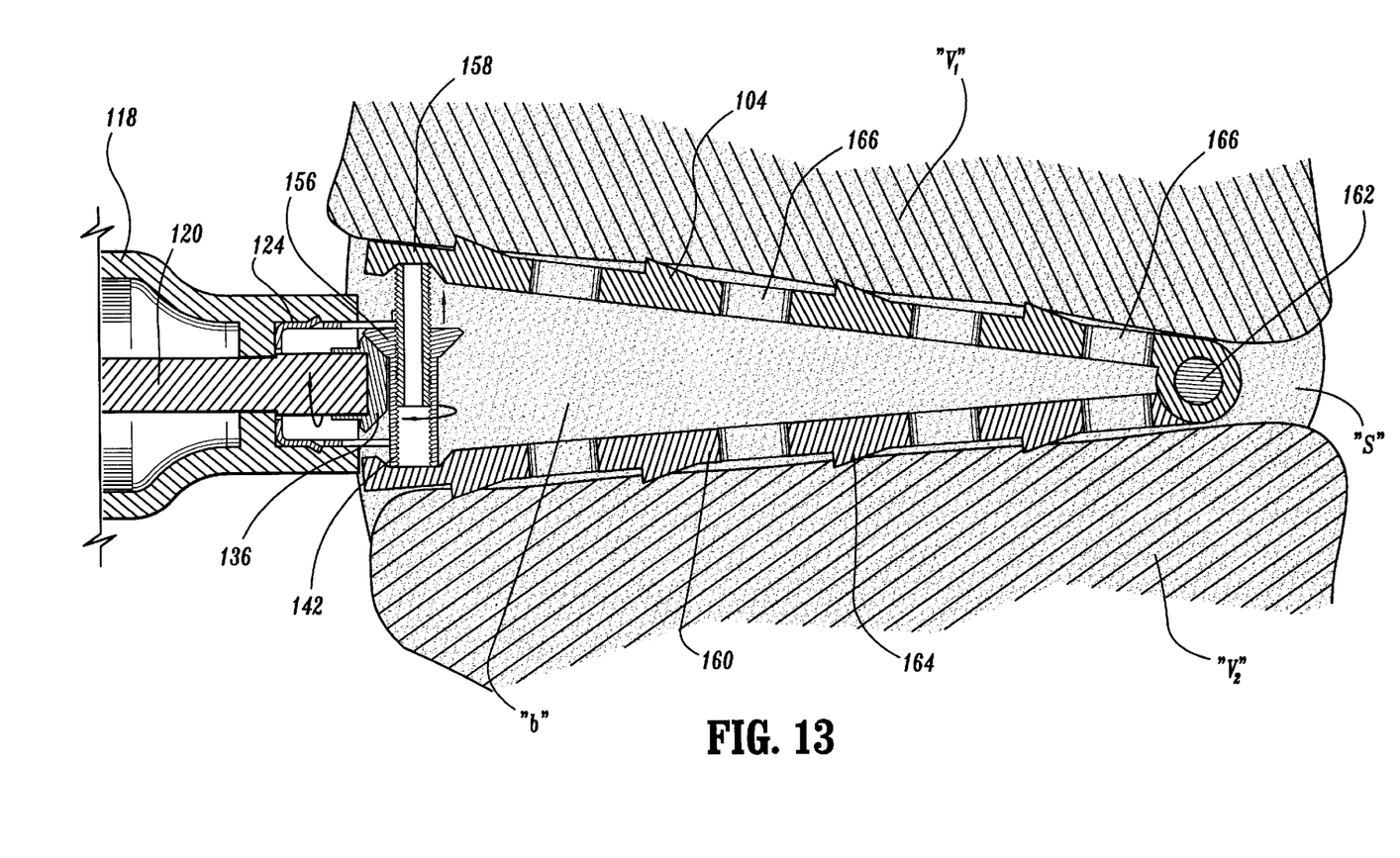
FIG. 13 is an enlarged cross-sectional view of the fusion implant disposed within the adjacent vertebrae with the displacement mechanism actuated to displace the vertebral engaging plates of the implant.

Referring now to FIG. 13, implant member 104 is illustrated in an open condition such that in engaging plates 158, 160 contact vertebral end plates of the adjacent vertebrae supporting engaged relation. In particular, to effect deployment of implant member 104, control knob 112 of applicator instrument 102 is rotated to cause corresponding rotation of deployment shaft 120 in the direction of the directional arrow shown in FIG. 13. Such movement of deployment shaft 120 causes rotation of spur gear 136 mounted to the distal end of the displacement shaft 120, which causes rotatable component 142 to rotate accordingly (as shown by the directional arrow of FIG. 13) due to the interaction of spur gear 156 of rotatable component 142 with spur gear 136. As rotatable component 142 rotates, jack screw 140 translates in the vertical direction through the interaction of the threaded components 144, 146 of the jack screw 140 and rotatable component 142 thereby causing engaging plates 158, 160 to pivot about pivot pin 162, (i.e., away from each other) and in engaged supporting relation with vertebrae $V_1$, $V_2$. In this deployed position, triangular projections 164 of upper and lower engaging plates 158, 160 penetrate and engage the vertebral end plates to securely fix the implant member 104 within the intervertebral space.

Figure 14:
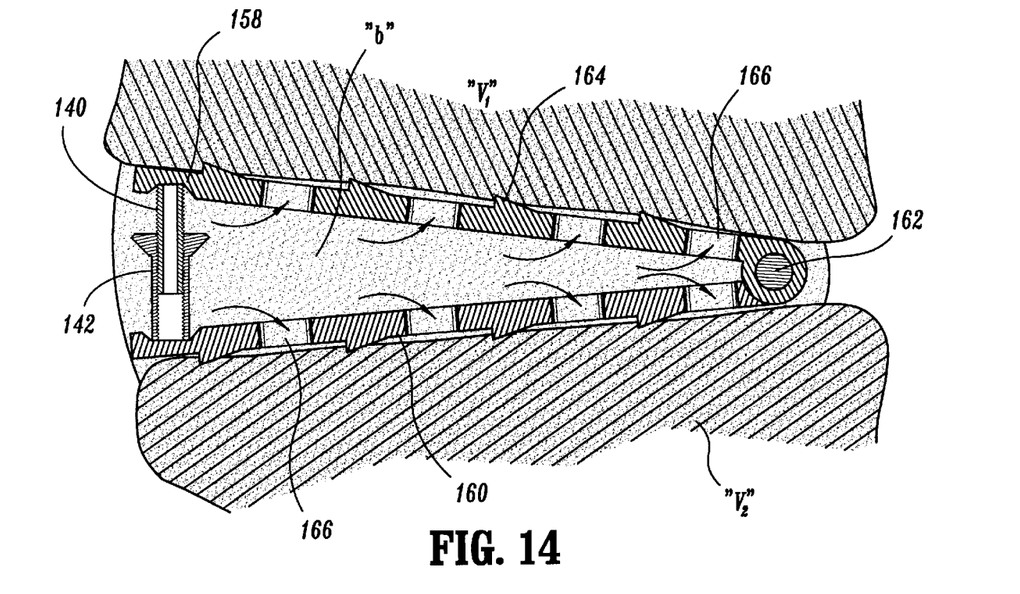
FIG. 14 is a view of the fusion implant deployed within the intervertebral space illustrating the communication of the bone growth inducing substances within the interior cavity of the fusion implant with the adjacent vertebral tissue.

Referring now to FIG. 14, with implant member forming a strut between adjacent vertebrae $V_1$, $V_2$, applier instrument 102 is removed leaving implant member 104 within the intervertebral space "s". Over a period of time, the adjacent vertebral tissue communicates through apertures 166 define in lower and upper engaging plates 158, 160 with the bone growth inducing substances "b" within interior cavity 168 of the implant to form a solid fusion.

Figure 15:
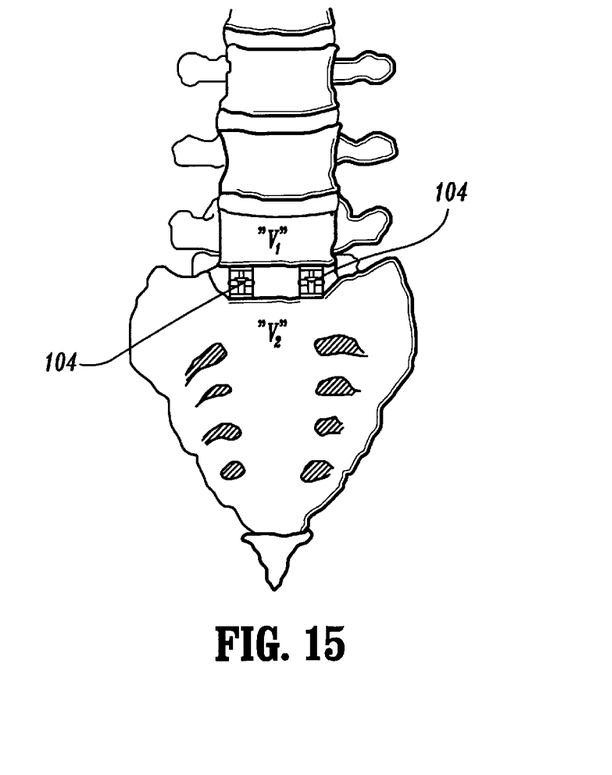
FIG. 15 is a view illustrating deployment of two fusion implants within the intervertebral space.

FIG. 15 illustrates two implant members 104 positioned in the intervertebral space of adjacent vertebrae $V_1$, $V_2$ to fully support the adjacent vertebrae $V_1$, $V_2$. The second implant member 104 is inserted in accordance with the method previously discussed.

Alternate Embodiment

Figure 16:
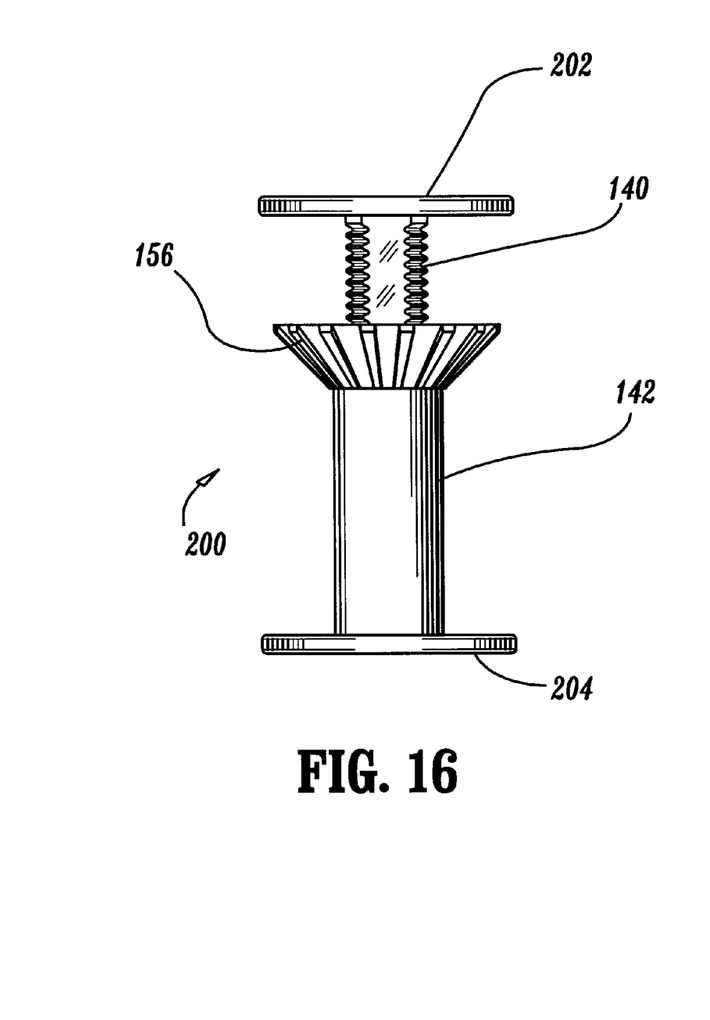
FIGS. 16–17 are views of an alternate embodiment of the fusion implant of FIG. 1.
Figure 17:
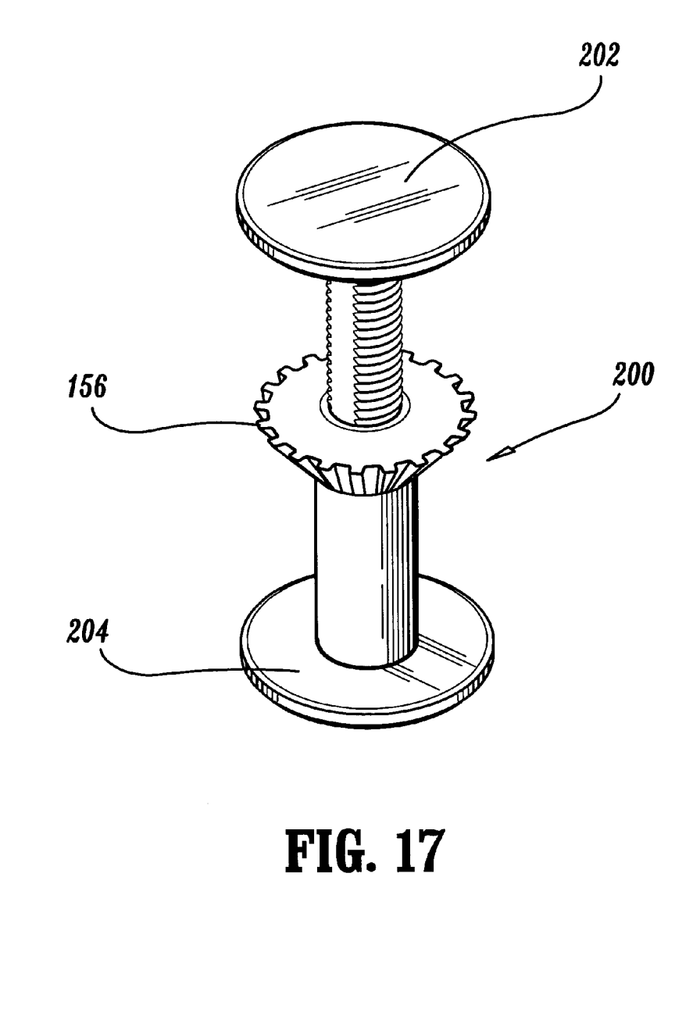

FIGS. 16–17 illustrate an alternate embodiment of the implant member of FIGS. 1–2. Implant member 200 is intended for use with the applier instrument 102 previously described. Implant member 200 is substantially similar to implant member 104, but, replaces pivotally mounted first and second engaging plates 158, 160, with support member 202, 204. More specifically, support member 202 is connected to jack screw 140 and support member 204 is connected to rotatable component 142. In a preferred embodiment, support members 202, 204 are integrally formed with their respective components. Jack screw 140 and rotatable component 142 are identical to those described in connection with the earlier embodiment and cooperate with mounting clamp 124 and spur gear 136 of applier instrument 102 in a similar manner, i.e., jack screw 140 and rotatable component 142 are received within rectangular recess 148 of upper plate 124a and arcuate recess 154 of lower plate 124b, respectively, to mount implant member 200 to the applier instrument. (FIG. 7) In addition, spur gear 156 of rotatable component 142 cooperates with spur gear 136 of applier instrument 102 to actuate and deploy implant 200.

Figure 18:
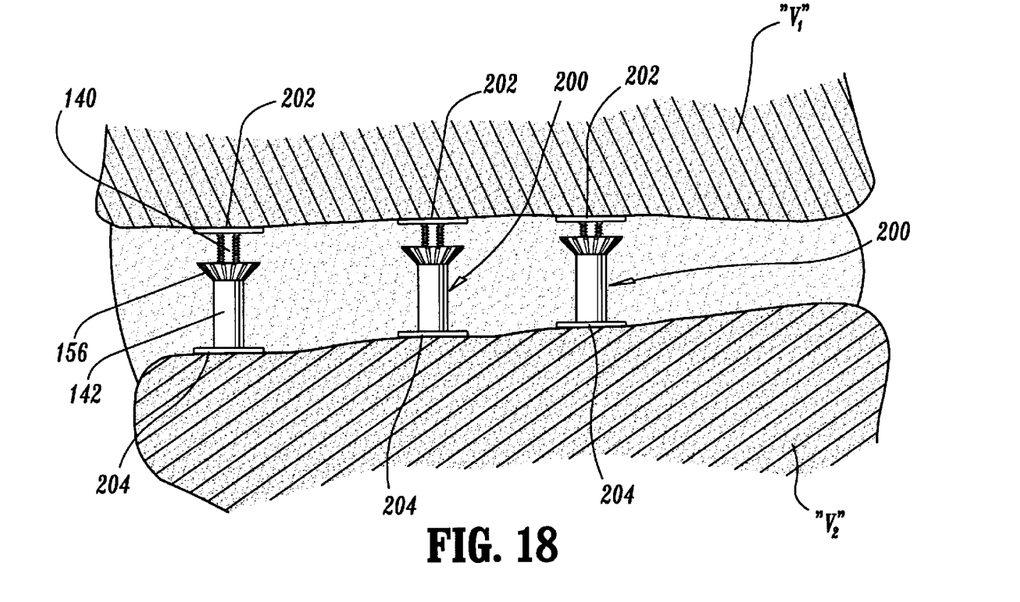
FIGS. 18–19 are view illustrating the implant of FIGS. 16–17 positioned within the intervertebral space.
Figure 19:
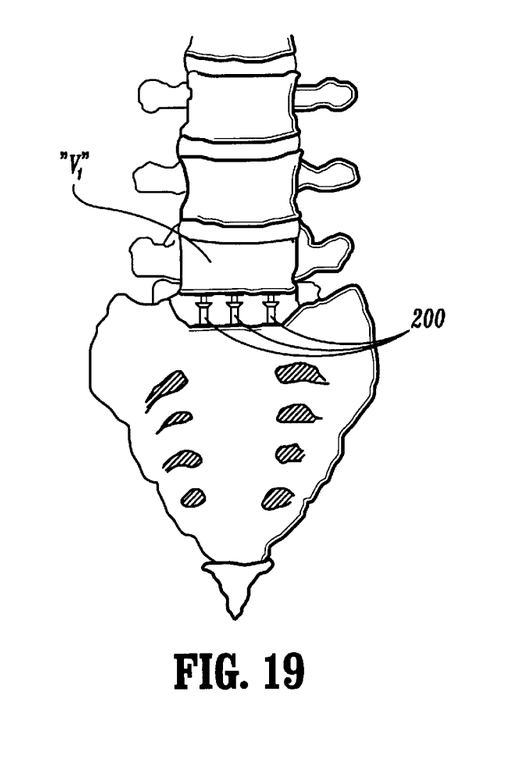

FIGS. 18–19 illustrate several, e.g., three, implant members 200 of the embodiment of FIGS. 16–17 deployed within the intervertebral space defined between adjacent vertebrae "$V_1$, $V_2$". As shown, support members 202, 204 engage the respective vertebral end faces to maintain the vertebrae "$V_1$, $V_2$" in spaced relation during healing. These implant members 200 are shown inserted within the adjacent vertebrae "$V_1$, $V_2$", however, it is envisioned that more or less implants 200 may be utilized depending on the desired objectives.

It is also contemplated that plates 202 and 204 can be eliminated and instead structure to bite into the bone, such as a sharpened edge or serrations, can be provided on the top of screw 140 and on the base of rotatable component 142.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A prosthetic implant apparatus for facilitating fusion of adjacent vertebrae, comprising an implant member dimensioned to be at least partially positioned within an intervertebral space defined between adjacent vertebrae, the implant member including first and second vertebral engaging plates pivotally connected to each other about a pivot pin extending through corresponding aligned openings of the first and second engaging plates, and adapted for relative pivotal movement to respectively engage vertebral surfaces of the adjacent vertebrae, the implant member defining a longitudinal median plane extending between the engaging plates in equidistant relation therewith, the first and second engaging plates having discontinuous surfaces to engage the vertebral surfaces and promote bone ingrowth, and a displacement member associated with the engaging plates and being movable in a transverse direction relative to the longitudinal median plane, to cause relative movement of the engaging plates, to thereby at least laterally displace the engaging plates to supportingly engage the adjacent vertebrae.

2. The apparatus according to claim 1 wherein the first and second engaging plates are pivotally connected to each other about the pivot pin at respective end portions thereof to define a reduced entry profile to facilitate insertion within the intervertebral space.

3. The apparatus according to claim 1 wherein the implant member defines an interior cavity for accommodating bone.

4. The apparatus according to claim 3 wherein the first and second engaging plates include apertures extending therethrough to permit communication with bone within the interior cavity.

5. The apparatus according to claim 4 wherein the first and second engaging plates include projections for engaging the vertebral end plates.

6. The apparatus according to claim 1 wherein the displacement member is a telescoping jack member, the telescoping jack member deployable with a remotely operable applier instrument.

7. The apparatus according to claim 6 wherein the telescoping jack member is a screw jack having a threaded portion cooperatively engageable with a threaded component wherein rotational movement of one of the screw jack and the threaded component causes corresponding telescoping motion of the screw jack and displacing movement of the first and second engaging plates.

8. The apparatus according to claim 7 wherein the threaded component is rotatable and has a spur gear associated therewith, the spur gear engageable with corresponding structure of an applier instrument.

9. An apparatus for facilitating fusion of adjacent vertebrae, which comprises:

an elongated member having proximal and distal ends and defining a longitudinal axis;

an implant member releasably mounted to the distal end of the elongated member, the implant member configured for insertion within an intervertebral space defined between adjacent vertebrae, the implant member including first and second separate and independent vertebral engaging plates pivotally connected to each other about a fixed pivot pin received within corresponding aligned openings defined in the first and second engaging plates, the first and second engaging plates adapted for relative pivotal movement between a retracted position and an extended position, the first and second engaging plates defining an internal cavity for reception of bone growth inducing substances and having contacting surfaces with apertures extending therethrough for communicating with the internal cavity; and a manually operable actuator operatively connected to the implant member, the actuator moveable to cause movement of the first and second engaging plates to the extended position thereof.

10. The apparatus according to claim 9 including a displacement mechanism associated with the implant member for moving the implant member to the extended position, the displacement mechanism operatively engageable with the actuator.

11. An apparatus for facilitating fusion of adjacent vertebrae, which comprises:

an elongated member having proximal and distal ends and defining a longitudinal axis;

an implant member releasably mounted to the distal end of the elongated member, the implant member configured for insertion within an intervertebral space defined between adjacent vertebrae, the implant member including first and second vertebral engaging plates pivotally connected to each other and adapted for relative pivotal movement between a retracted position and an extended position, the implant member defining a median longitudinal plane extending between the first and second engaging plates in equidistant relation therewith, the first and second engaging plates defining an internal cavity for reception of bone growth inducing substances and having contacting surfaces with apertures extending therethrough for communicating with the internal cavity and a spring operatively engageable with at least one of the first and second engaging plates to normally bias the implant member to the retracted position;

a displacement mechanism associated with the implant member for moving the implant member between the retracted and extended positions, the displacement mechanism being actuable in a direction having a transverse component relative to the longitudinal plane; and a manually operable actuator operatively connected to the displacement mechanism, the manually operable actuator adapted for rotational movement such that rotational movement of the actuator causes movement of the displacement mechanism to thereby move the implant member between the retracted and extended positions.

12. The apparatus according to claim 11 wherein the elongated member includes a drive shaft, the drive shaft operatively connected to the actuator and the displacement mechanism, the drive shaft adapted for rotational movement upon rotation of the actuator to thereby cause movement of the displacement mechanism and corresponding movement of the implant member between the retracted and extended positions.

13. The apparatus according to claim 12 wherein the displacement mechanism includes a telescopic jack disposed between the first and second engaging plates of the implant member and operatively engageable with the drive shaft, the telescopic jack adapted for telescoping motion to cause relative movement of the first and second engaging plates between the retracted and extended positions.

14. The apparatus according to claim 13 wherein the telescopic jack is a screw jack, the screw jack cooperating with a threaded component associated with the implant such that rotational movement of one of the screw jack and threaded component causes telescopic movement of the screw jack relative to the threaded component.

15. The apparatus according to claim 14 wherein the screw jack has a spur gear associated therewith, the spur gear cooperating with a spur gear associated with the distal end of the drive shaft such that rotation of the drive shaft causes corresponding rotation of each spur gear and telescopic movement of the screw jack.

16. An implant for facilitating fusion of adjacent vertebrae, comprising an implant member including first and second members pivotally connected and pivotally moveable relative to each other, and having first and second supporting surfaces for engaging respective vertebral surfaces of the adjacent vertebrae, the implant member defining a longitudinal median plane disposed between the first and second members in equidistant relation therewith, the first member having a threaded portion cooperatively engageable with a threaded portion of the second member, one of the threaded portions of the first and second members being rotatable about an axis which is generally transverse relative to the longitudinal plane to thereby cause corresponding relative movement of the first and second members through the cooperation of the respective threaded portions to thereby move the implant member to a deployed position wherein the first and second supporting surfaces are in oblique angular relation and contact the vertebral surfaces to maintain the adjacent vertebrae in predetermined spaced relation during healing.

17. The implant according to claim 16 wherein the first member includes an external threaded portion and the second member includes an internal threaded bore cooperatively engageable with the threaded portion of the first member to thereby cause relative movement of the first and second members upon rotation of the one of the first and second members.

18. The apparatus according to claim 1 wherein the first and second engaging plates are deployable to a deployed position such that contacting surfaces of the first and second engaging plates are in angular relation.

19. The apparatus according to claim 9 wherein the first and second engaging plates are in angular relation when in the extended position thereof.

20. A prosthetic implant for facilitating fusion of first and second adjacent vertebral portions, which comprises an implant member dimensioned to be at least partially positioned within an intervertebral space defined between adjacent vertebrae, the implant member including first and second separate and independent members pivotally connected about a fixed pivot pin extending through corresponding aligned openings of the first and second members, the first and second members having contacting surfaces for respectively engaging first and second adjacent vertebral portions, the first and second members pivotally movable about a fixed axis of rotation defined by the pivot pin from an initial position to facilitate insertion between the first and second vertebral portions to a deployed position wherein the contacting surfaces of the first and second members are in oblique angular relation and support the first and second vertebral portions in spaced relation.

21. The implant according to claim 20 wherein the first and second members each include apertures extending therethrough to permit communication with an interior space defined between the first and second members when in the deployed position thereof.

22. The apparatus according to clam 11 wherein the first and second engaging plates are pivotally connected about a pivot pin received within corresponding aligned openings of the first and second engaging plates.

23. The apparatus according to claim 16 wherein the first and second members are pivotally connected about a pivot pin.

24. The apparatus according to claim 23 wherein the pivot pin is stationary relative to the first and second engaging plates.

25. The apparatus according to claim 1 wherein the pivot pin is stationary relative to the first and second engaging plates.

26. The apparatus according to claim 22 wherein the pivot pin is stationary relative to the first and second engaging plates.

27. The apparatus according to claim 11 wherein the displacement mechanism is actuable in a transverse direction relative to the longitudinal plane.

28. A prosthetic implant for positioning between adjacent vertebrae, which comprises an implant member dimensioned to be at least partially positioned within an intervertebral space defined between adjacent vertebrae, the implant member including first and second members, each member having contacting surfaces for respectively engaging first and second adjacent vertebral portions, and means for pivotally mounting the first and second members to permit pivotal movement of the first and second members between an initial position to facilitate insertion between the first and second vertebral portions to a deployed position wherein the contacting surfaces of the first and second members are in oblique angular relation and support the first and second vertebral portions in spaced relation, wherein the means for pivotally mounting includes a pivot pin, the pivot pin defining a fixed axis of rotation, the first and second members being pivotally movable about the first axis of rotation of the pivot pin.

29. The prosthetic implant according to claim 28 wherein the pin is mounted with respect to the first and second members wherein movement of the first and second members is solely restricted to pivotal movement about the fixed axis of rotation.

\* \* \* \* \*